United States Patent
Petersen

(10) Patent No.: US 7,790,194 B2
(45) Date of Patent: *Sep. 7, 2010

(54) POLYACRYLAMIDE HYDROGEL AS A SOFT TISSUE FILLER ENDOPROSTHESIS

(75) Inventor: Jens Petersen, Birkerød (DK)

(73) Assignee: Contura A/S, Soborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/099,527

(22) Filed: Apr. 6, 2005

(65) Prior Publication Data

US 2005/0175704 A1 Aug. 11, 2005

Related U.S. Application Data

(62) Division of application No. 09/938,669, filed on Aug. 27, 2001.

(60) Provisional application No. 60/228,081, filed on Aug. 25, 2000.

(51) Int. Cl.
*A61F 2/02* (2006.01)

(52) U.S. Cl. .................. 424/423; 523/113; 523/114

(58) Field of Classification Search .............. 523/113, 523/114; 424/423, 426
See application file for complete search history.

(56) References Cited

U.S. PATENT DOCUMENTS

| | | | |
|---|---|---|---|
| 3,867,329 A | 2/1975 | Halpern et al. |
| 3,948,862 A | 4/1976 | Iwasyk |
| 4,074,039 A | 2/1978 | Lim et al. |
| 4,344,193 A | 8/1982 | Kenny |
| 4,502,161 A | 3/1985 | Wall |
| 4,535,131 A | 8/1985 | Handa et al. |
| 4,540,568 A | 9/1985 | Trager et al. |
| 4,540,569 A | 9/1985 | Ohnishi et al. |
| 4,571,749 A | 2/1986 | Fischell |
| 4,657,656 A | 4/1987 | Ogawa |
| 4,713,434 A | 12/1987 | Sutterlin et al. |
| 4,746,551 A | 5/1988 | Allen et al. |
| 4,857,041 A | 8/1989 | Annis et al. |
| 4,919,667 A | 4/1990 | Richmond |
| 4,969,474 A | 11/1990 | Schwarz |
| 5,135,480 A | 8/1992 | Bannon et al. |
| 5,171,322 A | 12/1992 | Kenny |
| 5,244,799 A | 9/1993 | Anderson |
| 5,306,404 A | 4/1994 | Notsu et al. |
| 5,344,451 A | 9/1994 | Dayton |
| 5,344,459 A | 9/1994 | Swartz |
| 5,482,719 A | 1/1996 | Guillet et al. |
| 5,516,532 A | 5/1996 | Atala et al. |
| 5,589,104 A | 12/1996 | Bambeck |
| 5,652,274 A | 7/1997 | Martin |
| 5,658,329 A | 8/1997 | Purkait |
| 5,667,778 A | 9/1997 | Atala |
| 5,700,289 A | 12/1997 | Breitbart et al. |
| 5,709,854 A | 1/1998 | Griffith-Cima et al. |
| 5,798,096 A | 8/1998 | Pavlyk |
| 5,813,411 A | 9/1998 | Van Bladel et al. |
| 5,854,382 A | 12/1998 | Loomis |
| 5,902,832 A | 5/1999 | Van Bladel |
| 5,941,909 A | 8/1999 | Purkait |
| 6,005,020 A | 12/1999 | Loomis |
| 6,060,053 A | 5/2000 | Atala |
| 6,129,761 A | 10/2000 | Hubbell |
| 6,252,016 B1 | 6/2001 | Wu et al. |
| 6,277,948 B1 | 8/2001 | Zahr |
| 6,335,028 B1 | 1/2002 | Vogel et al. |
| 6,486,213 B1 | 11/2002 | Chen et al. |
| 6,544,503 B1 | 4/2003 | Vanderhoff et al. |
| 6,592,859 B1 | 7/2003 | Bley |
| RE38,913 E | 12/2005 | Pavlyk |
| 7,186,419 B2 * | 3/2007 | Petersen ............... 424/423 |
| 2002/0064512 A1 | 5/2002 | Petersen et al. |
| 2002/0150550 A1 | 10/2002 | Petersen |
| 2002/0187172 A1 | 12/2002 | Reb et al. |
| 2003/0065389 A1 | 4/2003 | Petersen |
| 2003/0077244 A1 | 4/2003 | Petersen |
| 2003/0171509 A1 | 9/2003 | Balestrieri et al. |
| 2003/0176602 A1 | 9/2003 | Schmidt et al. |

FOREIGN PATENT DOCUMENTS

| | | |
|---|---|---|
| CN | 1228447 | 9/1999 |
| EP | 0153672 A2 | 9/1985 |
| EP | 0 248 544 | 12/1987 |

(Continued)

OTHER PUBLICATIONS

Gebauer et al., Gonarthritis due to *Salmonella enteritidis* in a patient with systemic lupus erythematosus, Klinische Padiatrie, (Sep.-Oct. 2002) 214 (5), 319-323, ABSTRACT.

(Continued)

*Primary Examiner*—Carlos A. Azpuru
(74) *Attorney, Agent, or Firm*—Hunton & Williams LLP

(57) ABSTRACT

A hydrogel is obtained by combining acrylamide and methylene bis-acrylamide, radical initiation and washing with pyrogen-free water or saline solution to give less than 3.5% by weight polyacrylamide, based on the total weight of the hydrogel. The hydrogel may be used as a soft tissue filler endoprosthesis. Also disclosed is a method of filling a soft tissue in a mammal using the endoprosthesis, and a prosthetic device comprising the polyacrylamide hydrogel.

26 Claims, No Drawings

FOREIGN PATENT DOCUMENTS

Figure 1:
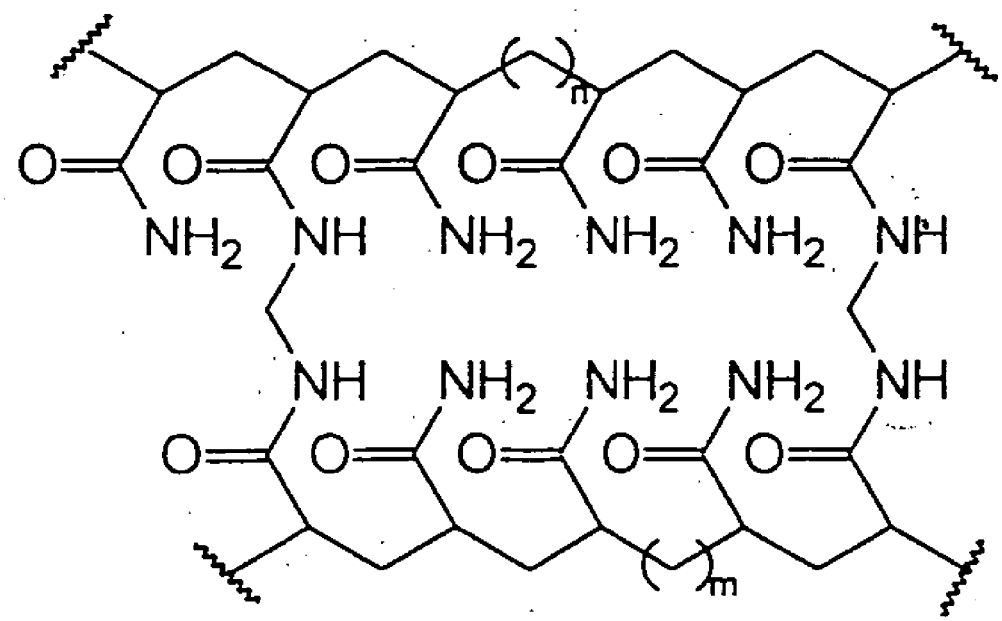

| | | |
|---|---|---|
| EP | 0153672 B1 | 5/1989 |
| EP | 0496067 A2 | 7/1992 |
| EP | 0555119 A1 | 8/1993 |
| EP | 0 826 381 | 3/1996 |
| EP | 0727232 A2 | 8/1996 |
| EP | 0 730 847 | 9/1996 |
| EP | 0727232 A3 | 11/1996 |
| EP | 0742022 A1 | 11/1996 |
| EP | 0 774 981 | 5/1997 |
| EP | 0 830 416 | 3/1998 |
| EP | 0727232 A * | 10/1998 |
| EP | 0 895 785 | 2/1999 |
| EP | 1 059 943 | 12/2000 |
| EP | 1 274 472 | 1/2003 |
| GB | 1317408 | 5/1973 |
| GB | 1320233 | 6/1973 |
| GB | 2114578 | 5/1981 |
| GB | 2114578 * | 8/1983 |
| RU | 2034465 | 5/1995 |
| RU | 2127129 | 3/1999 |
| RU | 2148957 | 5/2000 |
| SU | 1608193 | 11/1990 |
| SU | 1687291 | 10/1991 |
| SU | 1697756 A1 | 12/1991 |
| SU | 1831709 | 7/1993 |
| WO | WO81/01290 | 5/1981 |
| WO | WO89/07455 | 8/1989 |
| WO | 93/19702 | 10/1993 |
| WO | 96/04026 | 2/1996 |
| WO | WO96/04943 | 2/1996 |
| WO | 96/25129 | 8/1996 |
| WO | 96/39464 | 12/1996 |
| WO | 98/25575 | 6/1998 |
| WO | WO99/10021 | 3/1999 |
| WO | 99/15211 | 4/1999 |
| WO | 99/44643 | 9/1999 |
| WO | WO 00/31148 | 6/2000 |
| WO | 00/59411 | 10/2000 |
| WO | 00/78356 | 12/2000 |
| WO | WO 00/78356 | 12/2000 |
| WO | 01/32129 | 5/2001 |
| WO | WO 01/38402 | 5/2001 |
| WO | WO 01/42312 A1 | 6/2001 |
| WO | 01/47431 | 7/2001 |
| WO | 01/47433 | 7/2001 |
| WO | 01/50833 | 7/2001 |
| WO | WO 01/49336 A1 | 7/2001 |
| WO | 01/70289 | 9/2001 |

OTHER PUBLICATIONS

Jarosova et al., Analysis of clinical and laboratory data in a group of patients with juvenile idiopathic arthritis (JIA) in the framework of the national register, Ceska Revmatologie, (2002) 10/2 (65-70), ABSTRACT.

N.A. Peppas, 1986, *Hydrogels in Medicine and Pharmacy*.

Int'l Search Report dated Jan. 31, 2002 for Int'l Appl. No. PCT/DK01/00565 Filed Aug. 25, 2001.

Russian Federation, Irkutsk Region, Regional Licensing-Accreditation Commission, License Registration No. 94, (May 20, 1994) (Abstract).

Ministry of Public Health of Ukraine, Kiev Research Institute of Hematology and Blood Transfusion, Report dated Feb. 29, 1993.

Interfall's Biocompatible Hydrogel, Doctor's Information (Feb. 22, 2006) (citing U.S. Patent. No. 5,798,096) *at* http://www.bpg.bg/interfall/EB005140106biocompatible_gel1.htm.

Stevens, Malcolm P., Definitions, "Polymer Chemistry: An Introduction", Third Edition, Oxford University Press, Inc., Sect. 1.2, pp. 6-10, 1999.

Lewis, Richard J., Sr., Olefin (alkene), "Hawley's Condensed Chemical Dictionary", Thirteenth Edition, John Wiley & Sons, Inc., p. 819, 1997.

O'neil, Maryadele J., et al. (Eds.), Acrylamide, "The Merck Index: An Encyclopedia of Chemicals, Drugs, and Biologicals", Thirteenth Edition, Merck Research Laboratories, Merck & Co., Inc. No. 131, p. 128, 2001.

U.S. Appl. No. 11/469,213, filed Aug. 31, 2006, Petersen.

J.E. Gomez, and G.B. Thurston, Comparisons of the oscillatory shear viscoelasticity and composition of pathological synovial fluids, Biorheology, 30, 409-427 (1993).

\* cited by examiner

POLYACRYLAMIDE HYDROGEL AS A SOFT TISSUE FILLER ENDOPROSTHESIS

CROSS-REFERENCE TO RELATED APPLICATIONS

This application is a divisional application of U.S. patent application Ser. No. 09/938,669, filed Aug. 27, 2001, which claims the benefit, under 35 U.S.C. § 119(e), of Provisional Application No. 60/228,081, filed Aug. 25, 2000. Both applications are hereby incorporated by reference in their entirety.

FIELD OF INVENTION

The invention relates to a polyacrylamide hydrogel used as a prosthetic device for soft tissue augmentation such as facial cosmetic surgery, lip augmentation and soft tissue correction of the body. The hydrogel comprises less than 3.5% polyacrylamide solid weight content and pyrogen free water or saline solution.

BACKGROUND OF THE INVENTION

The success of plastic or reconstructive surgery depends to a great extent on the physical properties of the materials utilized. They must most certainly be biocompatible, stable and non-toxic but they must also have physical properties that mimic the bodily tissue they are replacing, as in reconstructive surgery, and mimic the bodily tissue in the proximity of the endoprosthesis, as in cosmetic surgery.

Natural and synthetic polymers such as collagen, soya, glycerol, silicone, polyvinylpyrolidone and hyaluronic acid have been utilized as endoprostheses. Materials used for endoprostheses generally try to imitate the natural soft tissue and are intended to be safe to the health of the patient. Materials such as collagen are re-absorbed into the body over short periods of time. Silicone and soya have encountered serious safety issues. There is currently a need for a safe, stable, biocompatible material that possesses the physical properties to mimic soft tissue.

Polyacrylamide gels have also been disclosed. WO 96/04943 relates to a biocompatible hydrogel containing 3.5 to 6.0% cross-linked polyacrylamide. However, WO 96/04943 teaches that concentrations below 3.5% make the hydrogel unstable.

GB 2114578 relates to a polyacrylamide gel for medical and biological purposes containing 3 to 28% polyacrylamide with the remainder of the mass of the gel comprised of a physiological solution. According to GB 2114578, the prospective utility in the polyacrylamide gel lies in the manufacture of artificial crystalline lenses (contact lenses), a dense base in growing microorganisms. GB 2114578 discloses the preparation of gels having 4.0 to 20.0%, 5.0 to 18.0% and 6.0 to 15.0% solid weight content.

U.S. Pat. No. 5,658,329 relates to an implantable endoprosthesis comprising a shell filled with a polyacrylamide gel comprising 2 to 20% polyacrylamide by weight and a viscosity range of 15 to 75 Pas.

Formacryl® polyacrylamide is a soft-tissue endoprosthesis consisting of 5% reticulated polyacrylamide polymer and 95% apyrogenic water commercialised as an injectable device for medical and dental use to correct congenital or acquired deficits such as wrinkles, lines and scars. It is to be implanted with a syringe in the hypodermis.

U.S. Pat. No. 5,306,404 relates to a process for preparing polyacrylamide gel plates for electrophoresis.

WO 99/10021 relates to an injectable, biocompatible hydrogel comprising 0.5 to 10% polyacrylamide and an antibiotic or antiseptic. WO 99/10021 is directed to the solving the problem of sappuration and rejection of the gel in its use an endoprosthesis.

SUMMARY OF THE INVENTION

In a first aspect, the invention relates to a hydrogel for use as a soft tissue filler endoprosthesis said hydrogel obtainable by combining acrylamide and methylene bis-acrylamide, radical initiation; and washing with pyrogen-free water or saline solution so as to give less than 3.5% by weight polyacrylamide, based on the total weight of the hydrogel.

In a second aspect, the invention relates to the use of a hydrogel comprising less than 3.5% by weight polyacrylamide, based on the total weight of the hydrogel, for the preparation of an endoprosthesis for soft tissue filling. Similarly, the invention relates to a method of filling soft tissue in a mammal comprising administering an endoprosthesis wherein the endoprosthesis comprises a hydrogel comprising less than 3.5% by weight polyacrylamide, based on the total weight of the hydrogel.

A further object of the invention is to provide a prosthetic device for soft tissue augmentation said device being injectable and comprising a polyacrylamide hydrogel said hydrogel being obtainable by combining acrylamide and methylene bis-acrylamide; radical initiation; and washing with pyrogen-free water or saline solution, so as to give less than 3.5% by weight polyacrylamide, based on the total weight of the hydrogel;

GENERAL DESCRIPTION OF THE INVENTION

The term "facial" in intended mean of relation to all areas of the face, such as but not exclusively, the cheeks, the jaw, the neck, the forehead, under the eyes, the head area, and the nose.

The term "body contouring" is intended to mean cosmetic or reconstructive surgery wherein soft tissue is augmented in order to correct a cosmetic or non-cosmetic defect in the soft tissue in the body, excluding the face, lips, breasts and penis. The present invention relates to facial corrections, lip augmentation, and body contouring.

The term hydrogel relates to the polyacrylamide polymer of the invention comprising less than 3.5% polyacrylamide and at least 95% pyrogen-free water or saline solution whereas the term endoprosthesis relates to the hydrogel present in the body.

The polyacrylamide hydrogel of the invention is obtainable by the polymerisation of the monomers acrylamide and N,N'-methylene-bis-acrylamide under radical initiation, followed by washing of the polymer with pyrogen-free water or saline solution. The washing of the polymer results in a swelling of the gel, due to absorption of the pyrogen-free water or saline solution by the polymer. The swelling of the hydrogel influences the solid weight content of the gel, i.e. the amount of polymeric material, polyacrylamide. The solid weight content of the hydrogel influences, at least in part, the physical (rheological) properties of the hydrogel and thus the ability to mimic human tissue when used as an endoprosthesis.

The present investigators have prepared a hydrogel having the desired Theological properties to act as a soft tissue filler endoprosthesis which is completely atoxic, stable, and non-resorbable. The present investigators have developed the hydrogel to be particularly amenable for use as an endoprosthesis for facial cosmetic or reconstructive surgery, for body contouring and for lip augmentation or reconstruction. The hydrogel of the present invention is not directed for use as an endoprosthesis for breast or penis augmentation.

A first aspect of the invention relates to a hydrogel for use as a soft tissue filler endoprosthesis said hydrogel obtainable by combining acrylamide and methylene bis-acrylamide in amounts so as to give less than 3.5% by weight polyacrylamide, based on the total weight of the hydrogel; radical initiation; and washing with pyrogen-free water or saline solution. Typically, the hydrogel is obtained by said combining acrylamide and methylene bis-acrylamide in a molar ratio of 150:1 to 1000:1. The hydrogel obtained in this manner has a structural formula as shown in FIG. 1, is sterile, has transparent or colourless appearance and has a pH in the range of 6.5 to 9.0, typically 7.0 to 9.0. Furthermore the hydrogel of the invention is stable to oxygen, high pressure, high and low temperatures, enzymes and bacteria.

The invention thus relates to the use of a hydrogel comprising less than 3.5% by weight polyacrylamide, based on the total weight of the hydrogel, for the preparation of an endoprosthesis for soft tissue filling. Given the hydrogel of the invention is directed for use as an endoprosthesis, it must be stable. Furthermore, given the hydrogel of the invention is directed for use as an endoprosthesis for selected parts of the human anatomy, the hydrogel typically comprises at least 0.5% by weight polyacrylamide, based on the total weight of the hydrogel, preferably at least 1.0% by weight polyacrylamide, more preferable at least 1.5% by weight polyacrylamide, such as at least 1.6% by weight polyacrylamide, based on the total weight of the hydrogel. Typically, the hydrogel of the present invention may have a solid weight content of 1.5, 1.6, 1.7 1.8, 1.9, 2.0, 2.1, 2.2, 2.3, 2.4, 2.5, 2.6, 2.7, 2.8, 2.9, 3.0, 3.1, 3.2, 3.3, 3.4, or 3.5% polyacrylamide, based on the total weight of the hydrogel.

In a preferred embodiment of the present invention, the hydrogel comprises about 1.9 to 2.9% by weight polyacrylamide, based on the total weight of the hydrogel. The hydrogel typically further comprises at least 95% by weight pyrogen-free water or saline solution, preferably pyrogen-free water. In a preferred embodiment, the hydrogel comprises at least 96% by weight pyrogen-free water or saline solution, preferably pyrogen-free water, more preferably at least 97% by weight pyrogen-free water or saline solution, preferably pyrogen-free water, such as 95%, 95.5%, 96%, 96.5%, 97%, or 97.5% by weight pyrogen-free water or saline solution, preferably pyrogen-free water.

A suitable saline solution has an osmolarity similar to that of interstitial fluid. Suitable saline solutions include but are not limited to the group selected from 0.25-1% aqueous sodium chloride, a Ringer-Lockart solution, an Earle solution, a Hanks solution, an Eagle medium, a 0.25-1% glucose solution, a potassium chloride solution, and a calcium chloride solution. In a preferred embodiment, the saline solution is an about 0.8-1% aqueous sodium chloride solution, such as a 0.8, 0.9 or 1% aqueous sodium chloride solution.

Pyrogen-free water or saline solution is used for the washing process. The washing process serves, in part, to remove all but trace amounts of the monomers acrylamide and N,N'-methylene-bis-acrylamide. These monomers are toxic to the patient as well as detrimental to the stability of the hydrogel. The washing process is preferably such that the concentrations of the monomers acrylamide and N,N'-methylene-bis-acrylamide are below 50 ppm, more preferably below 40 ppm, such as below 30 ppm, particularly preferably below 20 ppm, typically below 10 ppm, most preferably less than 5 ppm.

The solid weight content of the hydrogel of the present invention is essentially completely contributed by the polyacrylamide and N,N'-methylene-bis-acrylamide with residual contribution by the initiator. The hydrogel is substantially free of any other polymeric content.

As stated, the hydrogel of the invention is biocompatible, atoxic, non-allergenic, non-resorbable, chemically inert and stable to oxygen, high pressure, high and low temperatures, enzymes and bacteria. In the event that the hydrogel is exposed to excessive amounts of UV light, the physical features of the hydrogel are altered and is converted into a glue-like substance. Advantageously, this substance is also non-toxic.

Upon administration of the hydrogel, a thin layer of connective tissue surrounds the endoprosthesis, enabling the endoprosthesis to become a stable part of the connective tissue. Due to the bio-stability of the hydrogel and the thin layer of connective tissue, the endoprosthesis may be easily removed from the patient when placed in the subcutaneous area. This advantage is at least in part due to the stability of the hydrogel which in turn is at least in part due to the washing process.

Several factors affect the rheological properties of the hydrogel, such as the relative amount of monomer used, the relative amount of initiator, the temperature, the time of polymerisation, and other parameters of the polymerisation process, as well as the washing process. Thus, the polymerisation process may provide a hydrogel with an array of viscosities having a solid weight content of less than 3.5%. The invention is directed to a hydrogel as a soft-tissue filler endoprosthesis and thus the hydrogel preferably has a viscosity tailored to the soft-tissue it is intended to mimic. The hydrogel of the invention is typically for use as an injectable endoprosthesis for cosmetic or reconstructive surgery of the face, cosmetic or reconstructive surgery of the body (body contouring), and augmentation or reconstructive surgery of the lips.

The hydrogel of the invention may be injectable or implantable into the subcutaneous layer of the epidermis, preferably the hydrogel is injectable.

In one embodiment of the invention, the endoprosthesis is for use in facial cosmetic or reconstructive surgery and the hydrogel has a complex viscosity of about 2 to 100 Pas, preferably about 5 to 90 Pas, such as about 5 to 60 Pas, such as about 10 to 60 Pas. Most preferably, the endoprosthesis for use in facial cosmetic or reconstructive surgery was place by means of injection of the hydrogel.

Depending on the condition and region of the epidermis of the face where the soft-tissue filler is required (e.g. chin as opposed to cheek), the viscosity of the hydrogel may vary. Accordingly, the hydrogel may be for use in facial cosmetic or reconstructive surgery and have a complex viscosity of about 2 to 20 Pas, preferably about 2 to 18 Pas, such as about 2 to 15 Pas or 2 to 10 Pas, more preferably 2 to 7 Pas, most preferably 3 to 5 Pas.

In typical embodiments, the endoprosthesis may be for uses in correction of facial contour deformities due to aging, acne, trauma, surgery, infection or congenital deformities. The facial features typically in need of correction are, for instance, the cheekbones, nasolabial folds, glabellar frowns, depressed contours of the mouth, the chin, the size or shape the lips, as well as other soft tissue deficiencies of the face. The hydrogel restores the skin contours correcting soft tissue contour deformities of the face such as wrinkles and folds.

The hydrogel may serve for the preparation of an injectable hydrogel for lip enhancement or correct an array of aesthetic defects caused by congenital, traumatic or aging alterations.

As stated, invention relates to the use of the hydrogel for the preparation of an endoprosthesis for the filling of soft tissue filling selected from the soft tissue of the face and lips and soft tissue of the body. The hydrogel of the invention directed for use in the cosmetic or reconstructive surgery of the body (body contouring), preferably has a complex viscosity of about 5 to 50 Pas, preferably about 7 to 40 Pas, most preferably about 7 to 30 Pas.

In the embodiment wherein the hydrogel is used in the preparation of an endoprosthesis for lip augmentation or lip reconstruction the hydrogel preferably has a complex viscosity of about 2 to 10 Pas, more preferably 2 to 7 Pas, most preferably 3 to 5 Pas.

The elasticity module is an alternative physical characteristic of the hydrogel indicative, in part, of the degree of cross-linking of the hydrogel according to the present invention. Typically, the degree of cross-linking is such that the hydrogel has an elasticity module of not less than 10 Pa, such as not less than 25, 30, 31, 32, 33, 34 or 35 Pa, such as not less than 38 Pa. The gel may be characterized in that it has elasticity module from about 10 to 700 Pa, such as about 35 to 480 Pa.

A further object of the invention is to provide a prosthetic device for soft tissue augmentation said device being injectable and comprising a polyacrylamide hydrogel said hydrogel being obtainable by combining acrylamide and methylene bis-acrylamide in amounts so as to give less than 3.5% by weight polyacrylamide, based on the total weight of the hydrogel; radical initiation; and washing with pyrogen-free water or saline solution.

The prosthetic device of the invention preferably comprises a hydrogel comprising at least 0.5% by weight polyacrylamide, based on the total weight of the hydrogel, preferably at least 1% by weight polyacrylamide, more preferable at least 1.5% by weight polyacrylamide, such as at least 1.6% by weight polyacrylamide, based on the total weight of the hydrogel. Typically, the hydrogel comprises about 1.9 to 2.9% by weight polyacrylamide, based on the total weight of the hydrogel. The prosthetic device comprises the hydrogel which typically comprises at least 95% by weight pyrogen-free water or saline solution, preferably pyrogen-free water.

A further aspect of the invention relates to a method of filling soft tissue comprising administering an endoprosthesis wherein the endoprosthesis comprises a hydrogel comprising less than 3.5% by weight polyacrylamide, based on the total weight of the hydrogel. The hydrogel may be as described supra.

In an alternative embodiment of the invention, the prosthetic device comprises cells, such as stem cells. Polyacrylamide provides an excellent template and matrix for cell growth. Although the hydrogel of the invention allows, in itself, for a thin layer of connective tissue from the body of the patient to surround the device, the use of cells in combination with the hydrogel of the invention for the preparation of the device allows for cellular engraftment to the surrounding tissue.

The method of the invention typically comprises administering the hydrogel of the invention by injecting the hydrogel, into the subcutaneous layer of the skin in the embodiments wherein the endoprosthesis is for facial cosmetic or reconstructive surgery or body contouring. In the embodiment wherein the endoprosthesis is for lip augmentation or lip reconstruction, the injecting is above the muscle tissue of the lip.

The method may comprise of more than one injection so as to cover the desired area or to achieve the desired affect.

As stated, an alternative embodiment of the invention comprises administering the hydrogel of the invention in combination with cells, such as stem cells to allow for cellular engraftment of the prosthetic device.

The gel to be injected is typically stored in a syringe suitable for injecting the required amount for a single session treatment. Depending on the afflicted area, the amount of gel and thus volume of the syringe may vary, such as a syringe with a volume of 0.25-25 mL, such as a syringe selected from 0.5 mL, 0.7 mL, 1.0 ml, 1.5 mL. 2.0 mL, 2.5 mL, 5.0 mL, 7.5 mL, 10 mL, 12.5 mL. 15 mL, 20 mL and 25 mL. Obviously, the prosthetic device for use in facial surgery or lip augmentation be provided in a syringe in an array of volumes, typically lower in volume than the volumes provided for by the prosthetic device for body contouring. For instance, the device for lip augmentation may be provided in volumes of 0.5 ml or 0.7 mL or 1 mL whereas the device for body contouring may be provided in volumes of 2 mL, 5 mL, or 10 mL. These are purely illustrative examples and are not intended to limit the scope of the invention in any way—the device of the invention may be provided in any volume required to perform the method.

As stated, the hydrogel is highly biocompatible. The method of the invention does not comprise of adding an antibiotic, analgesic or anti-inflammatory agent to the hydrogel.

In the preferred embodiment wherein the method comprises the injection of the endoprosthesis, the injection comprises the use of a syringe with a thin gauge needle such as a 21-29 G needle. The necessary amount of the gel is injected subcutaneously in a retrograde manner by injecting the gel while withdrawing the needle. After the injection is performed, a light manipulation may be required in order to obtain an even distribution of the gel. Post-operative oedema may be treated with local packing of ice and mild pain and redness may be experienced during the first 2-3 days after injection.

In the embodiment wherein the method comprises injection of the endoprosthesis for lip augmentation or facial correction the needle of the syringe is typically particularly thin, such as a 25-29 G needle. For body contouring, the needle of the syringe may be in the range 21-23 G.

EXAMPLES

Example 1

Preparation of Hydrogel

The gel is a polyacrylamide gel manufactured by a polymerisation of the monomers of acrylamide and N,N'-methylene-bis-acrylamide. The finished product may have different viscosities.

The hydrogel has the empirical formula $[C_3H_5NO]_x$ $[C_7H_{10}N_2O_2]_y$ and the structural formula as shown in FIG. 1

The hydrogel typically contains approximately 95% water. The concentration of the monomers acrylamide and N,N'-methylene-bis-acrylamide has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers.

Preparation 1.1

The synthetic preparation suitably involves the following operations:
1. Two mixtures, A1 and A2, are prepared. A1 comprises water, acrylamide, N,N'-methylene-bis-acrylamide, N,N,N',N'-tetramethylene-ethylene-diamine (TEMED). A2 comprises water and ammonium persulphate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers;
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with an vertically oscillating grid;
8. The syringe is filled with the homogenised gel material;
9. Autoclavation of the syringe A typical method for preparing the hydrogel may be summarised as:

Preparation 1.2

Process summary. The gel is prepared by mixing an aqueous monomer solution of acrylamide and N,N'-methylene-bis-acrylamide as cross-linker with N,N,N',N'-tetramethylene ethylene diamine (TMED) as co-initiator and ammoniumpersulfate (APS) as free-radical initiator (redox-system). By degassing a bulk solution with nitrogen polymerisation starts. After final polymerisation the gel transferred into a washing tank with net trays onto which the gel is placed. During water washing the gel swells and monomer residues are extracted. The swollen gel is fed and evacuated in a filling unit having the gel delivered in a syringe, which is autoclaved.

Two alternate formulations have been prepared, a lower- and a higher-end viscosity formulation. Both formulations have a solid weight content of less than 3.5% and a complex viscosity in the range of 2 to 50 Pa s, typically between 3 and 20 Pa s.

TABLE 1

| Chemical constituent | lower end viscosity | higher end viscosity |
|---|---|---|
| acrylamide | 502 g | 547 g |
| N,N'-methylene-bis-acrylamide | 2.2 g | 4.6 g |
| TMED | 3.0 g | 2.6 g |
| APS | 5.4 g | 5.0 g |
| Non-pyrogenic water | Add 10 litre | Add 10 litre |

The above are typical preparations of the hydrogel and may be adjusted within certain ranges.

Preparation 1.3

Polyacrylamide Formulations from Inline Cross-Linking Process

A particularly interesting method of preparing the hydrogels of the invention involves an inline cross-linking process. Two individual and eventually degassed flows, one being a pre-mix of acrylic amide, bis-methylene acryl amide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high viscosity formulations. Hydrogels with solid weight contents between 0.5 and 25% polyacrylamide were prepared.

TABLE 2

Process parameters and features of resulting gel: low viscosity formulations

|  | lv1 | lv2 | lv3 | lv4 | lv5 | lv6 | lv7 $^d$ | lv8 $^e$ |
|---|---|---|---|---|---|---|---|---|
| washing time (hrs) | a) | 19.5 | 73.75 | 92 | 94.3 | 72.8 | 93.6 | 93.9 |
| dry matter$^f$ (%) | 2.55 | 2.08 | 2.63 2.36 2.58 2.09 | 2.87 2.67 | 2.89 2.82 | 3.15 2.90 | 3.68 3.57 | 3.17 3.52 |
| molar ratio AM:bisAM | b) | 976 | 700 | 488 | 366 | 3239 | 488 | 488 |
| molar ratio AM + BISAM: TEMED | 252 | 252 | 253 | 251 | 252 | 249 | 252 | 252 |
| molar ratio AM + BISAM: APS | 298 | 299 | 298 | 298 | 298 | 299 | 298 | 298 |
| residual monomer in ppm | c) | 89 | 5 | 2.97 | 2 | 5 | 1, 4 | 0.97 |

TABLE 2-continued

Process parameters and features of resulting gel: low viscosity formulations

| | | | | | | | | |
|---|---|---|---|---|---|---|---|---|
| elasticity G' in Pa | 0.16 | 5.23 | 14.3 20.1 | 26.6 | 57.05 | 71.7 | 39.2 | 28.5 |
| viscosity in Pa s | .045 | .88 | 2.35 3.30 | 4.37 | 9.1 | 11.5 | 6.29 | 4.55 |
| gelation time (min) | liquid | highly viscous liquid | 12 | 2 | 2 | 2 | 2.5 | 2.5 |

| | lv9 | lv10 | lv11 | lv11 | lv12 |
|---|---|---|---|---|---|
| washing time (hrs) | 121 | 96.4 | | | |
| dry matter (%) | 2.18 | (5.10)$^f$ | (10.2)$^f$ | (10.1)$^f$ | (20.2)$^f$ |
| molar ratio AM:bisAM | 701 | 701 | 488 | 488 | 488 |
| molar ratio AM + BISAM: TEMED | 252 | 252 | 252 | 504 | 2016 |
| molar ratio AM + BISAM: APS | 298 | 298 | 298 | 596 | 2385 |
| residual monomer in ppm | 0.97 | | | | |
| elasticity G' in Pa | 28.5 | 11.1 | (911)$^g$ | (1240)$^g$ | (9460)$^g$ |
| viscosity in Pa s | 4.55 | 1.8 | (145)$^g$ | (197)$^g$ | (1505)$^g$ |
| gelation time (min) | | 3.17 | 0.00 | 1.21 | 3.5 $^h$ |

$^a$material was liquid so washing was a dilution
$^b$infinite
$^c$since washing was not an extraction but a dilution, the residual monomer was merely decreased by the dilution factor (508 ppm to 254 ppm).
$^d$casting and washing done using 0.9% NaCl aqueous solution
$^e$casting with water; washing done using 0.9% NaCl aqueous solution
$^f$pre-wash values - washing typically reduces value by 30–55%
$^g$pre-eash values - washing typically reduces value by 20–40%
$^h$highly notch sensitive
$^i$variations in values may be due to measurement performance techniques or to location in the batch from which sample was taken

TABLE 3

Process parameters and features of resulting gel: medium viscosity formulations

| | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM: TEMED | 252 | 252 | 252 | 251 | 252 |
| molar ratio AM + BISAM: APS | 299 | 299 | 299 | 299 | 299 |
| residual monomer in ppm | 1.6 | | 1.5 | | |
| elasticity G' in Pa | 108.5 | | 129 | | 133.5 |
| viscosity in Pa s | 17.4 | | 20.6 | | 21.30 |
| gelation time (min) | 2.5 | 2.5 | 2.18 | | |

TABLE 4

Process parameters and features of resulting gel: high viscosity formulations

| | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + BISAM: TEMED | 315 | 315 | 604 | 313 | 314 |
| molar ratio AM + BISAM: APS | 376 | 376 | 755 | 375 | 376 |
| residual monomer in ppm | 0.2 | | | | |
| elasticity G' in Pa | 343 | 274 | | 314.5 | |
| viscosity in Pa s | 54.7 | 43.65 | | 50.1 | |
| gelation time (min) | 2.18 | 2.18 | 7.5 | | |

Example 2

Method of Administration
a) The injection of the gel may be performed under local anaesthesia, but for correction of wrinkles and folds, local anaesthesia is not necessarily required. For lip augmentation, anaesthesia through the nerve block is recommended.
b) The procedure must be performed under sterile conditions. Pharmaceuticals are not to be injected into the gel
c) The gel is pre-filled in sterile syringes of 1 mL with luer-lock and should be injected subcutaneously with a thin gauge needle, e.g 27 G. Needles should be CE-marked.
d) Inject the necessary amount of the gel subcutaneously in a retrograde manner by injecting the gel while withdrawing the needle. A patient record label is part of the packaging and is removable and to be attached to the patient record to ensure that the product is traceable.
e) After the injection is performed, a light manipulation may be performed in order to obtain an even or desired distribution of the gel. The injected gel will form a stable, soft part in the connective tissue and will give long lasting cosmetically satisfactory appearance.
f) Further injection sessions may be performed to achieve the desired affect.

Post-Operative Procedures

If oedema occurs, ice packs may be applied locally. Exposure to direct sunlight or extreme cold or heat is advised until the initial swelling and redness has been resolved.

Adverse Events/Side Effects

It is not uncommon for patients to develop some pain within the first 2-3 days post-operatively. A mild degree of oedema will occur in some patients during the first 2-3 days after injection.

The correct injection technique is crucial for the final result of the treatment and to be performed by authorised personnel.

The gel is sterilised (such as by moist heat or autoclavation). In the even that the package is damaged or opened but unused, sterility may be compromised and the contents should be discarded. Re-sterilisation is not advisable.

Example 3

Clinical Experience
1) Approximately 900 patients underwent facial corrections with the gel. The overall cosmetic results were excellent and the frequency or adverse events was 0.02% (Kovanskaya V. A.; Scienctific conference, 13-16 Oct. 2000).
2) A total of 150 adults undergoing correction of the contour deformities of the face were treated with the injectable gel. The amount of gel injected was from 0.2 to 11 mL.

Scheduled visits took place at a screening day (3 days prior to day 0), day 0 (first injection), day 7, day 28, month 3, month 6 and at end of study visit month 12 and underwent a physical examination and vital signs test, pregnancy test, blood and serum analysis, hematology test, immunology test, urine analysis, concomitant treatment, side effect and events analysis, cosmetic outcome analysis by patient and surgeon as well as completing a questionnaire according to the schedule of Table 5.

Results

The overall rating of the outcome of the surgery was from very good to good from both the patients and the surgeon. In some instances, the patients wanted to continue the treatment and receive further injections. Several surgeons remarked spontaneously on the questionnaire that the patients were happy with the result and that the gel was easy to handle and administer.

The gel was very well tolerated. Only a few side-effects were recorded and the Adverse Events oedema and inflammation were reported by the patient. The Adverse Events resolved spontaneously after a few days.

TABLE 5

|  | Screening (at least −3 days) | Day 0 (Facial correction) pre-op | Day 0 (Facial correction) post-op | Day 7 ±1 day | Day 28 ±2 days | month 3 ±7 days | month 6 ±7 days | month 12 ±7 days |
|---|---|---|---|---|---|---|---|---|
| information/informed consent | X | | | | | | | |
| physical examination | | X | | | | | X | X |
| vital signs | | X | | X | X | X | X | X |
| pregnancy test | | X | | | | | | |
| blood and serum analysis | sampling | X | | | | | X | X |
| Haematology | sampling | X | | | | | X | X |
| Immunology | sampling | X | | | | | X | X |
| Urine analysis | | X | | | | | X | X |
| Concomitant treatment | | X | X | X | X | X | X | X |
| side effects and events | | | X | X | X | X | X | X |
| questionnaire (complaints) | | | X | X | X | X | X | X |
| Cosmetic outcome | | | | | | | | |
| Patient | | | | | X | X | X | X |
| Surgeon | | | | | X | X | X | X |

The invention claimed is:

1. A method of filling soft tissue comprising administering a hydrogel as an endoprosthesis to an area in need thereof,
    said hydrogel comprising about 0.5 to less than 3.5% by weight polyacrylamide, based on the total weight of the hydrogel; wherein the polyacrylamide is crosslinked polyacrylamide;
    said hydrogel consisting essentially of a polymer of said crosslinked polyacrylamide,
    and at least 95% by weight pyrogen-free water or saline solution, and
    less than 50 ppm of acrylamide and methylene-bis-acrylamide monomers,
    and wherein the hydrogel has an elasticity module from about 10 to 700 Pa and a complex viscosity from about 2 to 100 Pas,
    and wherein said endoprosthesis consists essentially of said hydrogel.

2. The method according to claim 1, wherein the endoprosthesis does not comprise an antibiotic, analgesic or anti-inflammatory agent.

3. The method according to claim 1, wherein the hydrogel is obtainable by combining acrylamide and methylene bis-acrylainide in a molar ratio of 150:1 to 1000:1.

4. The method according to claim 1, wherein the hydrogel comprises at least 1.0% by weight polyacrylamide, based on the total weight of the hydrogel.

5. The method according to claim 1, wherein the hydrogel comprises from about 2.0 to 3.0% by weight polyacrylamide, based on the total weight of the hydrogel.

6. The method according to claim 1, wherein the soft tissue is soft tissue of the face; wherein the endoprosthesis is for facial cosmetic or reconstructive surgery; and wherein the hydrogel has a complex viscosity of about 2 to 20 Pas.

7. The method according to claim 1, wherein the soft tissue is soft tissue of the body; wherein the endoprosthesis is for cosmetic or reconstructive surgery of the body (body contouring), and wherein the hydrogel has a complex viscosity of about 5 to 50 Pas.

8. The method according to claim 1, wherein the soft tissue is soft tissue of the lip; wherein the endoprosthesis is for lip augmentation or lip reconstruction; and wherein said hydrogel has a complex viscosity of about 2 to 10 Pas.

9. The method according to claim 1, wherein the administering comprises injecting the hydrogel.

10. The method according to claim 9, wherein the endoprosthesis is for facial cosmetic or reconstructive surgery or body contouring and the injecting is into the subcutaneous layer of the skin.

11. The method according to claim 9, wherein the endoprosthesis is for lip augmentation or lip reconstruction and the injecting is above the muscle tissue of the lip.

12. The method according to claim 9, further comprising administering cells for cellular engrafment to the surrounding tissue.

13. The method according to claim 1, wherein the hydrogel comprises at least 1.5% and less than 3.5% by weight polyacrylamide, based on the total weight of the hydrogel.

14. The method according to claim 1, wherein the soft tissue is soft tissue of the face; wherein the endoprosthesis is for facial cosmetic or reconstructive surgery; and wherein the hydrogel has a complex viscosity of about 2 to 18 Pas.

15. The method according to claim 1, wherein the soft tissue is soft tissue of the face; wherein the endoprosthesis is for facial cosmetic or reconstructive surgery; and wherein the hydrogel has a complex viscosity of about 2 to 15 Pas.

16. The method according to claim 1, wherein the soft tissue is soft tissue of the face; wherein the endoprosthesis is for facial cosmetic or reconstructive surgery; and wherein the hydrogel has a complex viscosity of about 2 to 10 Pas.

17. The method according to claim 1, wherein the soft tissue is soft tissue of the face; wherein the endoprosthesis is for facial cosmetic or reconstructive surgery; and wherein the hydrogel has a complex viscosity of about 2 to 7 Pas.

18. The method according to claim 1, wherein the soft tissue is soft tissue of the face; wherein the endoprosthesis is for facial cosmetic or reconstructive surgery; and wherein the hydrogel has a complex viscosity of about 3 to 5 Pas.

19. The method according to claim 1, wherein the soft tissue is soft tissue of the body; wherein the endoprosthesis is for cosmetic or reconstructive surgery of the body (body contouring), and wherein the hydrogel has a complex viscosity of about 7 to 40 Pas.

20. The method according to claim 1, wherein the soft tissue is soft tissue of the body; wherein the endoprosthesis is for cosmetic or reconstructive surgery of the body (body contouring), and wherein the hydrogel has a complex viscosity of about 7 to 30 Pas.

21. The method according to claim 1, wherein the soft tissue is soft tissue of the lip; wherein the endoprosthesis is for lip augmentation or lip reconstruction; and wherein said hydrogel has a complex viscosity of about 2 to 7 Pas.

22. The method according to claim 1, wherein the soft tissue is soft tissue of the lip; wherein the endoprosthesis is for lip augmentation or lip reconstruction; and wherein said hydrogel has a complex viscosity of about 3 to 5 Pas.

23. The method according to claim 12, wherein the cells are stem cells.

24. The method according to claim 1, wherein the hydrogel has an elasticity module of not less than 25 Pa.

25. The method according to claim 1, wherein the hydrogel has an elasticity module of not less than 38 Pa.

26. The method according to claim 1, wherein the hydrogel has an elasticity module of about 35 to 480 Pa.

* * * * *